United States Patent [19]

Coughenour et al.

[11] Patent Number: 4,731,490

[45] Date of Patent: Mar. 15, 1988

[54] PROCESS FOR METHYL, TERTIARY BUTYL ETHER PRODUCTION

[75] Inventors: Glenn E. Coughenour, Bryn Mawr, Pa.; Joseph P. Chan, Cherry Hill, N.J.

[73] Assignee: Arco Chemical Company, Newtown Square, Pa.

[21] Appl. No.: 888,604

[22] Filed: Jul. 23, 1986

[51] Int. Cl.$^4$ ............................................. C07C 41/06
[52] U.S. Cl. ................................... 568/697; 568/699; 585/329
[58] Field of Search ................ 568/697, 699; 585/512, 585/329

[56] References Cited

U.S. PATENT DOCUMENTS

| | | | |
|---|---|---|---|
| 4,393,250 | 7/1983 | Gottlieb et al. | 568/697 |
| 4,504,688 | 3/1985 | Herwig et al. | 568/697 |
| 4,581,474 | 4/1986 | Watson et al. | 568/697 |

FOREIGN PATENT DOCUMENTS

| | | | |
|---|---|---|---|
| 2540488 | 8/1984 | France. | |
| 2121407 | 12/1983 | United Kingdom | 568/697 |

Primary Examiner—Howard T. Mars
Attorney, Agent, or Firm—Craig E. Larson

[57] ABSTRACT

A process for the production of methyl tertiary butyl ether comprising dimerizing ethylene to form a first butene-containing material; isomerizing the first butene-containing material to produce a second butene-containing material including an increased amount of isobutene relative to the first butene-containing material; and contacting at least a portion of the second butene-containing material with methanol at etherification conditions to produce an affluent enriched in methyl, tertiary butyl ether.

7 Claims, 3 Drawing Figures

PROCESS FOR METHYL, TERTIARY BUTYL ETHER PRODUCTION

BACKGROUND OF THE INVENTION

The present invention relates to an improved process for the production of methyl, tertiary butyl ether. More particularly, the invention relates to an efficient methyl, tertiary butyl ether production process utilizing selected feedstocks.

Methyl, tertiary butyl ether (MTBE) is widely used, e.g., as a gasoline blending component. Typically, MTBE is produced via the etherification of isobutene with methanol. The isobutene is normally provided to the etherification step in a feedstock mixture containing substantial concentrations of butanes and n-butenes, as well as isobutene. For example, the feedstock can be the raffinate from a conventional extractive distillation recovering butadiene from the effluent of a conventional $C_4$ dehydrogenation reactor system. Dienes and acetylenes are often present in the feedstock, particularly when it is derived from a dehydrogenation effluent.

The etherification reaction does not substantially convert the n-butenes. Straight chain olefins pass through the etherification system along with the butanes, dienes and acetylenes. Consideration has been given to isomerizing these residual n-butenes to isobutene and recycling the isomerate to etherification. However, the substantial build-up of butanes that would result in this recycle stream detrimentally affects the economics of such a processing option. Also, the presence of dienes and acetylenes in this recycle stream would be harmful to many of the isomerization catalysts that could be used to promote the n-butenes/isobutene isomerization.

The following reference materials have been reviewed in preparing this application: U.S. Pat. Nos. 4,329,516 and 4,555,312; Belgian Patent No. 887,125, and "The Changing Picture for $C_4$ Feedstocks", Chemical Week, Dec. 16, 1981. These materials disclose producing MTBE and/or pure butene-1, and the varying market for the individual $C_4$ hydrocarbons. There continues to be a need for an improved MTBE production process.

Accordingly, an object of this invention is to provide an improved process for the production of MTBE. Another object of the invention is to provide an MTBE production process with improved feedstock utilization and efficiency. More particular aspects, objects and the several advantages of this invention will become apparent to those skilled in the art upon reading this disclosure and the appended claims.

SUMMARY OF THE INVENTION

An improved process for the production of MTBE has been discovered. In one embodiment, the present process comprises: (1) contacting an ethylene-containing material at ethylene dimerization conditions to produce a first butene-containing material which includes less than about 10% by weight butane; (2) contacting the first butene-containing material at isomerization conditions to produce a second butene-containing material including an increased amount of isobutene relative to the first butene-containing material; and (3) contacting at least a portion of the second butene-containing material with methanol at etherification conditions to produce an effluent enriched in MTBE.

The present process provides outstanding advantages. MTBE is produced from ethylene rather than from conventional $C_4$ feedstocks. The relatively low initial butane concentration in the first butene-containing material allows an effective, e.g., economically viable, recycle operation in which n-butenes which are not converted in step (3) can be recycled to step (2). The first, ethylene dimerization, step may be conducted so that the first butene-containing material includes very small concentrations, preferably less than about 100 ppm by weight, if any, of each of dienes and acetylenes. This minimizes, and will often eliminate, the need to hydrotreat the recycle stream, i.e., n-butene-containing material from step (3), prior to subjecting this recycle stream to step (2). One particularly useful aspect of the present process is its use in conjunction or combination with an existing MTBE production system utilizing a typical butene/butane feedstock, e.g., a raffinate from extractive distillation to recover butadiene and/or other $C_4$ compounds. The present process acts to enrich such typical feedstocks in butenes, thereby making recycle operation more economically practical and increasing the MTBE yield based on total butenes in the process.

DETAILED DESCRIPTION OF THE INVENTION

Figure 1:
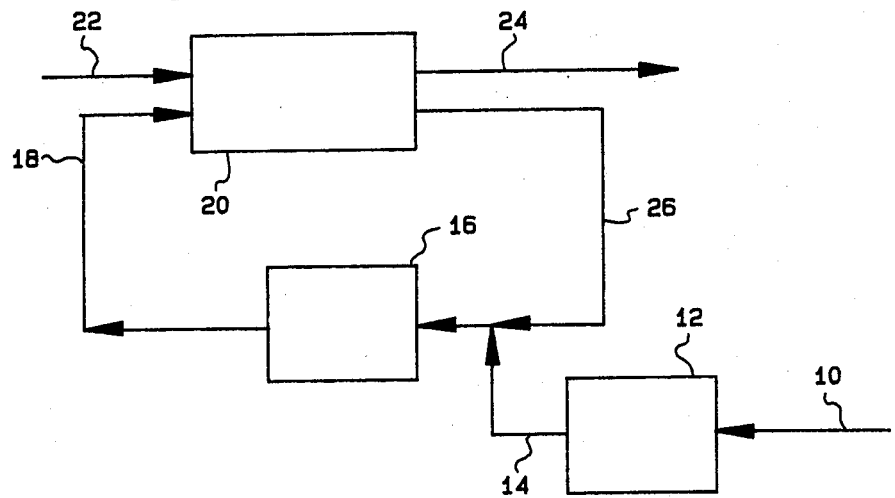

The present process utilizes a first butene-containing material produced by ethylene dimerization, i.e., by contacting an ethylene-containing material at ethylene dimerization conditions. Preferably, the dimerization product contains less than about 10% by weight butane, more preferably less than about 5% by weight and still more preferably less than about 1% by weight butane. Most preferably, the first butene-containing material is substantially free of butane.

The ethylene dimerization step may be chosen from any suitable ethylene dimerization process. Such processes are conventional and well known in the art. The ethylene dimerization is preferably promoted by a catalyst. Homogeneous or heterogeneous catalysts may be employed. If heterogeneous catalyst is employed, the catalyst can be disposed as fixed, moving, fluidized, or ebullating beds. Dimerization conditions, e.g., temperature, residence time or space velocity, pressure, and the like, are chosen based on the feedstocks and catalyst being employed and on the desired product composition. Such conditions preferably include reaction temperatures in the range of about −10 degrees C. to about 100 degrees C. and reaction pressures in the range of subatmospheric to 100 atmospheres. These conditions are preferably chosen to provide relatively high yields of butene. The overall yield of butene (based on ethylene converted in the dimerization step) will typically be at least about 50%, preferably at least about 70% and more preferably at least about 90%. The feedstock to the dimerization process step is preferably polymerization grade ethylene. This feedstock contains at least 80%, preferably at least about 90% and more preferably at least about 95%, by weight ethylene.

Many dimerization catalyst systems may be employed in the present invention. The particular catalyst chosen is not critical to the present invention. For example, the catalyst can be organic aluminum compounds organic titanium compounds and mixtures thereof. See U.S. Pat. No. 4,532,370 and French Patent No. 2,540,488. Other examples include: alkyl or aryl aluminum halides; mixtures of titanium oxy alkyls or aryls and aluminum alkyls; cobalt or nickel complexes containing various ligands; rhodium chloride; palladium chloride/hydrogen chloride mixtures; and iridium chloride/alcohol systems.

The first butene-containing material is contacted at isomerization conditions to produce a second butene-containing material including an increased amount of isobutene relative to the first butene-containing material. In other words there is a net production of isobutene by subjecting the first butene-containing material to isomerization conditions. The isomerization process step is preferably promoted by a catalyst. Any suitable skeletal isomerization catalyst, e.g., capable of promoting the isomerization of at least one n-butene to isobutene at isomerization conditions, may be employed. Care should be taken to avoid undue losses of butene to saturation, polymerization and the like during this isomerization. Preferably, at least about 80%, more preferably at least about 90% and still more preferably at least about 95%, of the butene entering the isomerization step, i.e., step (2) of the present process, exits the isomerization step as butene.

Included among the suitable isomerization catalysts are those well known in the art. Many of the isomerization catalysts possess at least a limited amount of acidity. Preferably, the catalyst is provided in the form of solid particles in a fixed, moving, fluid, or ebullating beds. One particular class of solid isomerization catalysts are halogen-, especially chlorine- and fluorine-containing alumina. Specific examples of this class include fluorided or chlorided alumina and fluorine/boron trifluoride/alumina catalysts. Molecular hydrogen and/or halogens, organic halides and hydrogen halides may be present, e.g., added periodically or continuously, during the isomerization contacting if such presence is beneficial, e.g., to facilitate prolonging the effective life or maintaining the catalytic activity of the isomerization catalyst.

Isomerization conditions are preferably chosen to provide the desired degree of butene isomerization and, more preferably, to inhibit butene saturation of polymerization. Preferred isomerization temperatures are in the range to about 200 degrees C. to about 500 degrees C., more preferably about 250 degrees C. to about 450 degrees C. Pressures are preferably in the range of subatmospheric to about 75 psia, more preferably about 10 psia to about 20 psia.

The specific composition of the isomerization catalyst and the isomerization conditions are not critical to the present invention.

The second butene-containing material is contacted with methanol at etherification conditions to produce an effluent enriched in MTBE. This isobutene/methanol etherification is well known and is described, for example in U.S. Pat. Nos. 2,480,940; 3,037,052; and 3,281,475. Preferably, this second butene-containing material is catalytically etherified with methanol, the isobutene being almost quantitatively converted to MTBE, while the remainder of the second butene-containing material experiences no conversion and leaves the etherification reactor substantially unchanged. Generally, the etherification takes place in the liquid phase, preferably at temperatures in the range of about 30 degrees to 100 degrees C., more preferably about 60 degrees to 90 degrees C. and pressures in the range of about 2 to 24, more preferably about 10 to 22, atmospheres. The pressure is selected to keep the components in the reaction mixture in liquid phase during the reaction. The molar ratio of methanol to isobutene is preferably maintained in the range of about 1 to 2:1, more preferably in the range of about 1:1 to 1.4:1. In a continuous, catalytic operation, the volume hourly space velocity is preferably in the range of about 0.5 to about 20.

The etherification reaction preferably occurs in the presence of an acid catalyst, e.g., sulfuric acid, sulfonic acid, hydrofluoric acid, aluminum chloride, boron fluoride and the like. More preferred catalyst include materials containing —$SO_3H$ groups, such as sulfonated charcoals like Nalcite X and AX, and Zero-Karb-H; sulfonated phenol-formaldehyde resins like Amerlite IR-100 and Nalcite MX; sulfonated cumarone-indene polymers; and sulfonated polystyrene-divinylbenzene resins like Dowex 50, Nalcite HCR and Amberlyst 15. Catalysts for etherification can include, for example, sulphonated ion exchange resins arranged as a solid bed, such as those which have frequently been described for this reaction, e.g., in German Offenlegungsschrift No. 26 20 011.

A methyl, tertiary butyl ether product is recovered from the effluent of the etherification raction system, e.g., using conventional techniques such as fractional distillation. The unreacted n-butenes from the second butene-containing material may be recycled to step (2) to produce additional isobutene for the etherification step. This butene recycle can be performed with improved efficiency since the first butene-containing material of the present process has only a limited butane content. Thus, the butene recycle can be accomplished without an undue build-up in the butane content of the recycle stream. Additionally, the first butene-containing material and the recyle stream contain only very minor amounts, if any, of dienes and acetylenes which can detrimentally affect the isomerization step and/or catalyst. Thus, the recycle can be accomplished without removal (e.g., by selective hydrogenation) of such dienes and acetylenes from the first butene-containing stream or the above-noted recycle stream.

In one embodiment of the present invention, it has been found that the present first butene-containing material, with limited butane concentration, can be processed in conjunction with a third butene-containing material, having a higher butane concentration (relative to the first butene-containing material) to provide an improved MTBE process. This third butene-containing material preferably is derived from the raffinate of an extractive distillation of a $C_4$ hydrocarbon-containing material to produce a butadiene product. Since such raffinates often contain a substantial concentration of isobutene, it is preferred to direct such raffinates directly to etherification, as described above, to produce MTBE.

In one particular embodiment, the second butene-containing material, described previously, in combined with a separate isobutene-containing material, e g., the raffinate described above, and this mixture is fed to the etherification step, described above, for the production of MTBE. At least a portion, more preferably substantially all, of the $C_4$ hydrocarbon-containing effluent from the etherification is subjected to step (2), i.e., isomerization conditions, preferably together with the first butene-containing material to produce a second butene-containing material including an increased amount of isobutene relative to the mixture or combination. This second butene-containing material is then subjected to step (3), as described above.

In situations where the third butene-containing material includes an amount (e.g., more than about 10 ppm by weight) of at least one diene and/or acetylene, the third butene-containing material is preferably contacted with hydrogen at selective hydrogenation condtions to reduce the amount of at least one of the diene and acetylene prior to subjecting the third butene-containing material to step (2). Such selective hydrogenation may be particularly appropriate when the third butene-rich material is derived from a butadiene extraction distillation raffinate.

When required, selective hydrogenation of diene and acetylene hydrocarbons is preferably carried out in the presence of a noble metal (especially Pd) catalyst. The catalyst may be associated with a support (e.g., alumina, silica, spinel, charcoal and mixtures thereof). A catalyst with about 0.01% to about 2% by weight palladium on alumina is particularly preferred. The conditions at which the selective hydrogenation occurs depends, for example, on the catalyst being used, and are chosen to provide the desired diene/acetylene hydrogenation without substantial hydrogenation of the butenes present. Preferably, the selective hydrogenation temperature is in the range of about −10 degrees C. to about 100 degrees C., more preferably about 0 degrees C. to about 40 degrees C.

Figure 2:
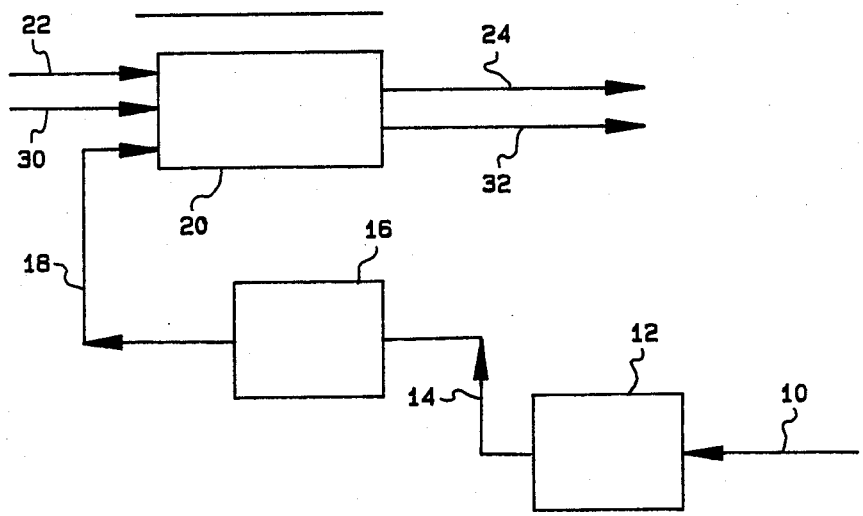
Figure 3:
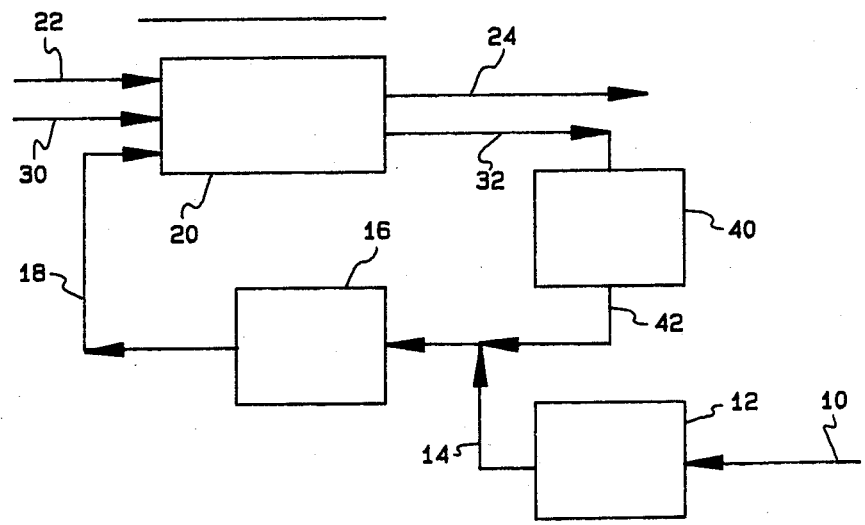

Certain embodiments of the present invention are described below with reference to the accompanying drawings in which:

FIGS. 1, 2 and 3 are schematic flow diagrams of three different embodiments of the present invention.

Referring now to FIG. 1, ethylene derived from conventional thermal pyrolysis of a mixture of naphtha and gas oil is fed via line 10 to a dimerization zone 12. An n-butene rich product is produced and passes through line 14 to isomerization zone 16. This n-butene rich product contains more than 95% by weight n-butenes, less than 1% by weight butanes and is substantially free of dienes and acetylenes.

Isomerization zone 16 is adapted to skeletally isomerize n-butenes to isobutene. The isobutene-enriched material from isomerization zone 16 is fed by line 18 to an etherification zone 20. Methanol from line 22 is also fed to etherification zone 20. MTBE product is recovered from etherification unit 20 and removed by line 24. An isobutene-depleted C4 hydrocarbon material from etherification zone 20 is fed by line 26 to isomerization zone 16. Normal butenes in this isobutene-depleted C4 hydrdocarbon material are skeletally isomerized to isobutene in isomerization zone 16.

This recycle operation, e.g., recycle to extinction, provides for improved overall yields of MTBE based on butene in the feedstock to etherification zone 20. The fact that the ethylene dimer product has a reduced butane concentration allows this recycle operation to be conducted without high build-ups of substantially inert butane in the recycle loop. Also, since substantially no dienes or acetylenes are present, the skeletal isomerization of n-butenes in isomerization zone 16 can be performed without requiring a separate step to selectively hydrogenate these materials.

FIGS. 2 and 3 illustrate two embodiments in which the n-butene rich product from dimerization zone 12 is used in conjunction with an isobutene-containing hydrocarbon stream derived from sources other than dimerization zone 12. FIGS. 2 and 3 are described with reference to C4 hydrocarbon raffinate derived from extractive distillation to recover a butadiene product, but other isobutene-containing streams, such as C4 streams from FCC units, may be employed. The raffinate, which includes more butane and isobutene than does the n-butene rich product from dimerization zone 12, is fed by line 30 into etherification zone 20. The mixture of raffinate and isobutene enriched material from line 18 is reacted with metnanol from line 22 to form a MTBE product which is removed by line 24 and an isobutene-depleted C4 hydrocarbon material which leaves etherification zone 20 by line 32.

In the embodiment illustrated in FIG. 2, the isobutene-depleted C4 hydrocarbon material in line 32 is not recycled back to the etherification zone 20, but is sent to further processing, e.g., separation, product blending and the like.

In the embodiment illustrated in FIG. 3, the isobutene-depleted C4 hydrocarbon material in line 32 is fed to selective hydrogenation zone 40 where dienes and acetylenes in this material are hydrogenated. The substantially diene/acetylene-free C4 hydrocarbon material from selective dehydrogenation zone 40 in line 42 is combined with the n-butene rich product in line 14 and fed to isomerization zone 16. Normal butenes in the material from line 42 is skeletally isomerized to isobutene and fed by line 18 to etherification zone 20. Both the materials in lines 32 and 42 have increased butane contents relative to the n-butene-rich material in line 14.

While this invention has been described with respect to various specific examples and embodiments, it is to be understood that the invention is not limited thereto and that it can be variously practiced within the scope of the following claims.

What is claimed:

1. A process for the production of methyl, tertiary butyl ether comprising:
    (a) dimerizing ethylene to produce a first butene-containing material which includes less than about 1% by weight butane;
    (b) isomerizing said first butene-containing material to produce a second butene-containing material including an increased amount of isobutene relative to said first butene-containing material; and
    (c) contacting at least a portion of said second butene-containing material with methanol at etherification conditions to produce an effluent enriched in methyl, tertiary butyl ether.

2. The process of claim 1 wherein step (b) comprises contacting a mixture of said first butene-containing material and at least a portion of a third butene-containing material having an increased butane concentration relative to said first butene-containing material at isomerization conditions to produce a second butene-containing material including an increased amount of isobutene relative to said mixture.

3. The process of claim 1 which further comprises (d) separating said effluent to recover a methyl, tertiary butyl ether product and byproduct comprising unreacted butenes and (e) returning said unreacted butenes to step (b).

4. The process of claim 1 wherein a third butene-containing material is fed with the second butene-containing material to the etherification step (c).

5. The process of claim 4 wherein said third butene-containing material includes an amount of at least one of at least one diene and at least one acetylene.

6. The process of claim 5 wherein the third butene-containing material is contacted with hydrogen at selective hydrogenation conditions to reduce the amount of at least one of said diene and said acetylene in said butene-containing material prior to step (c).

7. The process of claim 5 wherein the effluent from step (c) is separated to recover a methyl, tertiary butyl ether product and byproduct comprising unreacted butenes and at least one member of the group consisting of dienes and acetylenes; the byproduct is contacted with hydrogen at selective hydrogenation conditions to reduce the amount of said dienes and acetylenes; and selectively hydrogenated byproduct is combined with the first butene-containing material isomerized in step (b).

* * * * *